US008319602B2

(12) United States Patent
Pommi

(10) Patent No.: US 8,319,602 B2
(45) Date of Patent: Nov. 27, 2012

(54) APPARATUS HAVING A TRANSPONDER ENABLED MOVEABLE COMPONENT AND METHOD FOR CONTROL THEREOF

(75) Inventor: Doris Pommi, Herzogenaurach (DE)

(73) Assignee: Siemens Aktiengesellschaft, München (DE)

( * ) Notice: Subject to any disclaimer, the term of this patent is extended or adjusted under 35 U.S.C. 154(b) by 901 days.

(21) Appl. No.: 12/148,097

(22) Filed: Apr. 16, 2008

(65) Prior Publication Data

US 2008/0258866 A1 Oct. 23, 2008

(30) Foreign Application Priority Data

Apr. 20, 2007 (DE) ......................... 10 2007 018 811

(51) Int. Cl.
*G05B 19/12* (2006.01)
*G08B 29/00* (2006.01)
*G08B 21/22* (2006.01)
*A61B 6/10* (2006.01)

(52) U.S. Cl. ................... 340/5.31; 340/5.61; 340/572.1; 5/600

(58) Field of Classification Search ................. 340/5.61, 340/5.6, 5.2, 572.1, 5.31; 5/600, 601, 607, 5/608, 609, 610, 611, 612, 613, 614, 616, 5/617, 618, 619, 640, 634, 635, 81.1 R, 83.1, 5/85.1, 87.1, 88.1, 86.1, 84.1, 81.1 C, 81.1 RF, 5/81.1 HS
See application file for complete search history.

(56) References Cited

U.S. PATENT DOCUMENTS 6,205,952 B1 * 3/2001 Forster ............................ 119/71
6,247,343 B1 * 6/2001 Weiss et al. ..................... 70/277
6,825,752 B2 * 11/2004 Nahata et al. ................ 340/5.64
7,154,397 B2 * 12/2006 Zerhusen et al. .......... 340/573.1
7,331,071 B1 * 2/2008 Cherubini et al. ............... 5/83.1
7,769,218 B2 * 8/2010 Crucs ............................ 382/132
2001/0032405 A1 * 10/2001 Kaminski .................... 42/70.05
2001/0042332 A1 * 11/2001 Gering et al. ................ 42/70.08
2003/0006649 A1 * 1/2003 Budzynski .................... 307/10.2
2003/0016122 A1 * 1/2003 Petrick ....................... 340/10.41
2004/0104271 A1 * 6/2004 Martucci et al. ......... 235/472.01
2005/0128184 A1 * 6/2005 McGreevy .................... 345/156
2005/0154431 A1 * 7/2005 Quistgaard et al. ............. 607/96
2005/0172398 A1 * 8/2005 Smith et al. .................. 5/81.1 R
2006/0025897 A1 * 2/2006 Shostak et al. .................... 701/1
2006/0055510 A1 * 3/2006 Little et al. ................... 340/5.62
2006/0058913 A1 * 3/2006 Andersen et al. ............. 700/214
2006/0066453 A1 * 3/2006 Homanfar et al. ......... 340/686.2
2006/0075558 A1 * 4/2006 Lambarth et al. ................. 5/611
(Continued)

FOREIGN PATENT DOCUMENTS

DE 4317240 A1 12/1994
(Continued)

*Primary Examiner* — Benjamin C Lee
*Assistant Examiner* — Stephen Burgdorf

(57) ABSTRACT

In the field of medical devices, for instance patient tables, it is known to block the movement of moveable components of a respective apparatus using blocking means and to release these only after actuating a switch. To be able to dispense with the foot switch, an authorized operator is equipped with a radio frequency identification tag and interrogation means for interrogating the radio frequency identification tag are provided on the apparatus. Once the operator initiates a movement by exerting a force, a sensor detects this force and activates the interrogation means. If the interrogation means identify that the radio frequency identification tag is sufficiently close thereto, it is concluded that the authorized operator would like to initiate the movement and the moveable part is released.

6 Claims, 1 Drawing Sheet

U.S. PATENT DOCUMENTS

2006/0213996 A1* 9/2006 Crucs ....................... 235/462.13
2006/0219049 A1* 10/2006 Horvath et al. ................. 74/560
2007/0008152 A1* 1/2007 Parias ........................ 340/573.1
2007/0169268 A1* 7/2007 Lemire et al. ..................... 5/617
2007/0186923 A1* 8/2007 Poutiatine et al. ....... 128/200.14
2008/0245867 A1* 10/2008 Mynhardt ................ 235/462.01
2009/0043253 A1* 2/2009 Podaima ......................... 604/67
2009/0052618 A1* 2/2009 Homanfar et al. .............. 378/38
2009/0115610 A1* 5/2009 Steinhage et al. ......... 340/572.1

FOREIGN PATENT DOCUMENTS

DE 19945208 A1 4/2001
DE 102005021604 A1 11/2006
WO 2007005507 A2 1/2007

* cited by examiner

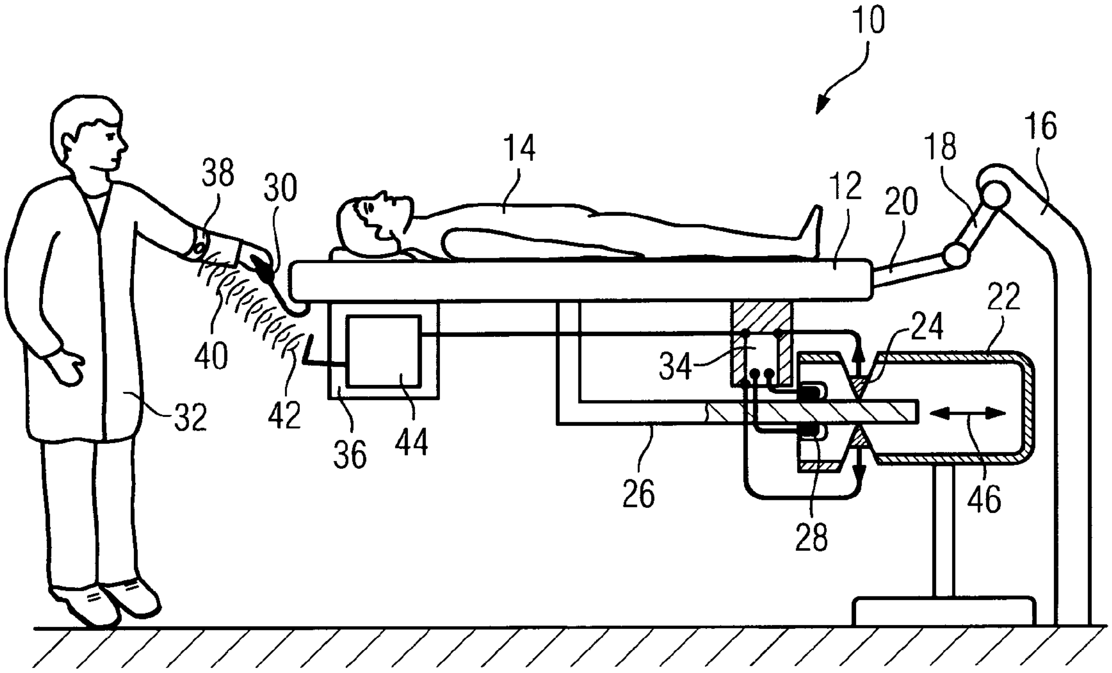
10
14
16
18
38
30
12
20
22
24
34
40
42
32
36
44
26
28
46

APPARATUS HAVING A TRANSPONDER ENABLED MOVEABLE COMPONENT AND METHOD FOR CONTROL THEREOF

CROSS REFERENCE TO RELATED APPLICATIONS

This application claims priority of German application No. 10 2007 018 811.2 filed Apr. 20, 2007, which is incorporated by reference herein in its entirety.

FIELD OF THE INVENTION

The invention relates to an apparatus with a moveable component. The invention is motivated in the field of medical engineering by necessity, in which moveable components (of superstructural parts or devices) are not to be moveable by just anyone, but instead only by an authorized operator, e.g. the treating physician. Accordingly, the invention also relates to a method for enabling the movement of a moveable part only by means of an authorized operator.

BACKGROUND OF THE INVENTION

During the treatment of patients, it is frequently necessary to move the patient table such that the treating physician is positioned optimally in respect of the patient. It is also necessary in the case of other superstructural parts such as for instance (3D) ceiling stands for an x-ray tube or an x-ray detector for the physician or the x-ray assistant for instance to be able to perform optimum adjustments as fast as possible by means of few hand movements. On the other hand however, the patient must be prevented from influencing the moveable components on his/her part, be this by accidental unintentional movements or deliberately. For this reason, the movement of moveable components in the field of medical apparatuses, in other words medical superstructural parts, frames and devices, is frequently blocked. A switch, for instance a foot switch, must be actuated by the treating physician so as to release the blockage. The actuation of the switch distracts the physician from his/her treating task, and is unergonomic and time-consuming.

SUMMARY OF THE INVENTION

It is thus the object of the invention to specify an apparatus with a moveable component, in which only an authorized operator, and not an unauthorized operator, is able to move the moveable component. A method for enabling the movement of a moveable component only by means of an authorized operator is also to be provided.

The object is achieved by an apparatus and a method having the features of the claims.

The apparatus with a moveable component, as known from the prior art, has a blocking facility controlled by a control unit, which prevents a (namely any) movement of the moveable component in an initial state. In the case of the apparatus according to the invention, a foot switch is however herewith unnecessary such that interrogation means are provided in order to determine whether a portable automatically interrogatable identification object is located at a predetermined minimum distance from the interrogation means. To this end, the control unit is suitably designed here not to terminate the initial state, as long as a portable automatically interrogatable identification object is not located at the predetermined minimum distance.

Only the authorized operator, in other words the physician for instance, need now carry a portable automatically interrogatable identification object. The blocking facility at least prevents any movement of the moveable component as long as the authorized operator does not sufficiently approach the interrogation means and thus the apparatus. It thus no longer possible, as in the prior art, to identify the authorized operator by actuating a switch; he/she can instead move naturally. The portable interrogatable identification object can be located in a shirt pocket of the authorized operator or also arranged on an armband.

The sole precondition for releasing the blockage of the moveable component by the blocking facility is preferably not that the portable automatically interrogatable identification object be located at a predetermined minimum distance. Instead, an additional prerequisite can be provided in that a force effect is actually exerted on the moveable component. Provision is then made with the inventive apparatus for a sensor, which detects a force effect on the moveable component. The control unit is to then be designed not to terminate the initial state, as long as the sensor does not detect any force effect.

Indeed, provision can be made that for interrogation means as well as the sensor to be constantly active, or only the interrogation means can be constantly active, and the sensor is then activated when the predetermined minimum distance of the portable automatically interrogatable identification object is detected. The simplest solution is however for only the sensor to be constantly active, this being readily possible in the case of a simply structured pressure sensor. Only when the sensor detects a force effect on the moveable component are the interrogation means activated (for which purpose a potentially superordinate control entity or the control unit has to be suitably designed). The potentially more complicated interrogation means operating as the sensor then detect whether or not an initiated movement of the moveable component was caused by an authorized operator.

All known techniques and techniques still to be developed are suitable as interrogation means, above all wirelessly operating techniques, such as infrared transmission, Bluetooth technology or also radio frequency. The use of relatively far advanced techniques of identifying radio frequency identification tags (so-called RFID tags) is particularly advantageous. The apparatus must then include a radio transmit/receive facility for detecting a radio frequency identification tag and the authorized operator must then wear the radio frequency identification tag, if necessary with the aid of a suitable means like an armband or a chain for instance. In the case of the radio frequency identification tag technology, the radio transmit/receive facility emits radio waves with a code. The radio frequency identification tag reflects the radio wave emissions back to the radio transmit/receive facility. It is possible to conclude the position of a radio frequency identification tag, which matches the emitted code in the vicinity of the apparatus, from the fact that radio wave emissions are actually received back. The reflected radio output is optionally also a measure for the distance. For simplification purposes, a threshold value can be used: if the reflected output exceeds a threshold power, it is assumed that the authorized operator is not sufficiently close to the apparatus and in particular to the moveable component.

The apparatus according to the invention can include a moveable patient table. To this end, it can represent a suitable device or device system, in which the patient is positioned. In terms of its functionality, the apparatus can also focus solely on the positioning of a patient.

The apparatus according to the invention also preferably includes a (preferably three-dimensionally pivotable) ceiling stand, for instance for an x-ray tube and/or an x-ray detector.

The method according to the invention for enabling the movement of a moveable part only by means of an authorized operator includes the steps:

blocking the movement of the moveable component with the aid of a blocking facility, equipping an authorized operator with a portable automatically interrogatable identification object, detecting whether a force is exerted on the moveable component, and if this is the case:

interrogating the portable automatically interrogatable identification object using assigned interrogation means and only if the identification object of the authorized operator is detected as being located at a minimum distance from a reference object (and/or is actually detected when the interrogation means is equipped differently):

controlling the blocking facility in order to release the movement of the moveable component (according to the control by the authorized operator).

BRIEF DESCRIPTION OF THE DRAWINGS

A preferred embodiment of the invention is described below with reference to the drawing, with the only FIGURE schematically illustrating an apparatus according to the invention.

DETAILED DESCRIPTION OF THE INVENTION

A patient table apparatus illustrated in the FIGURE and designated as a whole with 10 includes a patient table 12, on which a patient 14 is shown here lying down. The patient table 12 is held in a stable position with the aid of a freely configurable mechanism. A holding frame 16 is shown by way of example and only schematically, with two articulated arms 18 and 20 which can be pivoted in respect of each other, on which the patient table 12 is suspended. The patient table 12 can alternatively be positioned hydraulically or pneumatically for instance.

The movement of the patient table 12 essentially enabled by the articulated arms 18 and 20 is blocked by a brake 24 arranged in a holding element 22 as a blocking facility, which engages here with an appendage 26 of the patient table 12. A sensor 28 is also arranged in the holding facility 22, which detects whether a force is exerted on the patient table 12. The sensor 28 is a conventional pressure-sensitive sensor for instance. A handle 30, which can be actuated by an operator 32, is located on the patient table 12, and is also actuated in the situation shown in the FIGURE. The sensor 28 detects a pressure exerted by the operator 32 and sends a corresponding signal to a control unit 34. The control unit 34 thereupon activates a radio transmit/receive facility 36. The radio transmit/receive facility 36 is able to identify radio frequency identification tags located in its vicinity. Here the operator 32 wears an armband 38 with a radio frequency identification tag of this type. The radio transmit/receive facility 36 sends electromagnetic radiation 40 with a code which matches the radio frequency identification tag 38 and the radio frequency identification tag 38 sends a part 42 of this radiation back to the radio transmit/receive facility 36. The radio transmit/receive facility 36 includes an evaluation facility 44, which evaluates the incoming signals which match the code defined thereby. If it follows that the radio frequency identification tag 38 is located in the vicinity of the radio transmit/receive facility 36, as shown in the FIGURE, it is concluded on the basis of the receipt of reflected signals 42 or if these exceed a predetermined power, that by wearing the radio frequency identification tag 38, it is recognized as an authorized operator, who actuates the handle 30. The evaluation unit 44 forwards a corresponding item of information to the evaluation unit 34 and this controls the blocking elements 24 such that the appendage 26 is no longer blocked and the patient table 12 is moved according to the wishes of the operator 32.

In the embodiment shown in the FIGURE, a to and fro movement according to the double arrow 46 is possible. The invention is however not restricted to linear movements, but can be used in all apparatuses of this type, in which any movement patterns are possible. Such apparatuses can be patient table apparatuses, but however also completely different apparatuses, which are not shown in the FIGURE, stand designs for instance.

The invention claimed is:

1. An apparatus, comprising:

a medical device including a moveable component supported by freely articulable arms, which is adjustable to medically treat a patient;

wherein the moveable component comprises either a moveable patient table or a ceiling stand for an x-ray tube or an x-ray detector;

a portable automatically interrogatable identification object;

an interrogation unit coupled to the medical device, the interrogation unit normally inactive and when activated is arranged to detect whether the portable automatically interrogatable identification object is located within a predetermined minimum distance from the interrogation unit;

a blocking unit that prevents the moveable component from moving, comprising a brake that acts on an appendage of the medical device to prevent the moveable component from moving;

a pressure sensor affixed to the appendage, the sensor arranged to detect a force effect on the moveable component, wherein the sensor is constantly active and the interrogation unit is activated in response to a detection by the sensor of the force effect on the moveable component; and a control unit that controls the blocking unit to permit the movement of the movable component only if the portable automatically interrogatable identification object is located within the predetermined minimum distance.

2. The apparatus as claimed in claim 1, wherein the portable automatically interrogatable identification object is a radio frequency identification tag.

3. The apparatus as claimed in claim 2, wherein the interrogation unit comprises a transmitter/receiver for detecting the radio frequency identification tag.

4. The apparatus as claimed in claim 1, wherein the portable automatically interrogatable identification object is carried on an authorized operator of the apparatus.

5. A method for controlling a movement of a moveable component of an apparatus by an authorized operator, comprising:

providing a medical device including the moveable component supported by freely articulable arms, which is adjustable to medically treat a patient;

wherein the moveable component comprises either a moveable patient table or a ceiling stand for an x-ray tube or an x-ray detector;

equipping the authorized operator with a portable automatically interrogatable identification object;

arranging an interrogation unit to be normally inactive;

when the interrogation unit is activated, detecting if the portable automatically interrogatable identification object is located within a minimum distance from a reference object;

affixing a pressure sensor to an appendage of the moveable component;

arranging the sensor to be constantly active for detecting a force effect on the moveable component;

activating the interrogatable identification object in response to a detecting by the sensor of the force effect on the moveable component; and controlling a blocking unit comprising a brake that acts on the appendage of the medical device to permit the movement of the moveable component only if the portable automatically interrogatable identification object is located within the minimum distance from the reference object.

6. An apparatus, comprising:

a medical device including a moveable component supported by freely articulable arms, which is adjustable to medically treat a patient;

wherein the moveable component comprises either a moveable patient table or a ceiling stand for an x-ray tube or an x-ray detector;

a portable automatically interrogatable identification object;

an interrogation unit coupled to the medical device, the interrogation unit constantly active to detect whether the portable automatically interrogatable identification object is located within a predetermined minimum distance from the interrogation unit;

a blocking unit that prevents the moveable component from moving, comprising a brake that acts on an appendage of the medical device to prevent the moveable component from moving;

a pressure sensor affixed to the appendage, the sensor normally inactive and when activated is arranged to detect a force effect on the moveable component, wherein the sensor is activated in response to a detection by the interrogation unit of the interrogatable identification object being located within the predetermined minimum distance; and a control unit that controls the blocking unit to permit the movement of the movable component only when the portable automatically interrogatable identification object is located within the predetermined minimum distance and the sensor detects the force effect on the moveable component.

* * * * *